United States Patent
Huza et al.

(10) Patent No.: US 8,133,310 B2
(45) Date of Patent: Mar. 13, 2012

(54) METHOD AND APPARATUS FOR IN-SITU TESTING OF FILTRATION SYSTEMS

(75) Inventors: Mark Huza, Columbia, MD (US); Thomas C. Morse, Greenville, NC (US)

(73) Assignee: Camfil Farr, Inc., Riverdale, NJ (US)

( * ) Notice: Subject to any disclaimer, the term of this patent is extended or adjusted under 35 U.S.C. 154(b) by 0 days.

(21) Appl. No.: 13/205,587

(22) Filed: Aug. 8, 2011

(65) Prior Publication Data

US 2011/0290120 A1 Dec. 1, 2011

Related U.S. Application Data

(63) Continuation of application No. 12/163,384, filed on Jun. 27, 2008, now Pat. No. 7,998,252.

(60) Provisional application No. 60/947,198, filed on Jun. 29, 2007.

(51) Int. Cl.
*B01D 46/00* (2006.01)
*B01D 35/147* (2006.01)

(52) U.S. Cl. ............. 96/413; 96/417; 55/309; 55/385.2; 55/481

(58) Field of Classification Search ............. 95/273, 95/278, 281; 96/399, 404, 413, 417; 55/309, 55/385.2, 478, 481
See application file for complete search history.

(56) References Cited

U.S. PATENT DOCUMENTS

| | | | |
|---|---|---|---|
| 7,658,787 B2 * | 2/2010 | Morse et al. | 95/273 |
| 7,758,664 B2 * | 7/2010 | Morse et al. | 55/385.2 |
| 7,896,938 B2 * | 3/2011 | Morse et al. | 55/385.2 |
| 2009/0044600 A1 * | 2/2009 | Morse | 73/38 |

* cited by examiner

*Primary Examiner* — Robert Clemente
(74) *Attorney, Agent, or Firm* — Patterson & Sheridan, LLP

(57) ABSTRACT

Embodiments of the invention generally provide an apparatus and method for certifying a filter in a containment system without decontaminating the containment system prior to certification. The apparatus generally comprises a valve assembly selectable between at least three operational states. A first state prevents flow from prevents flow through a port of a housing. A second state fluidly couples the port to test equipment necessary to test a filter disposed within the housing. A third state seals the port but fluidly couples the test equipment to a decontamination system.

19 Claims, 4 Drawing Sheets

FIG. 1

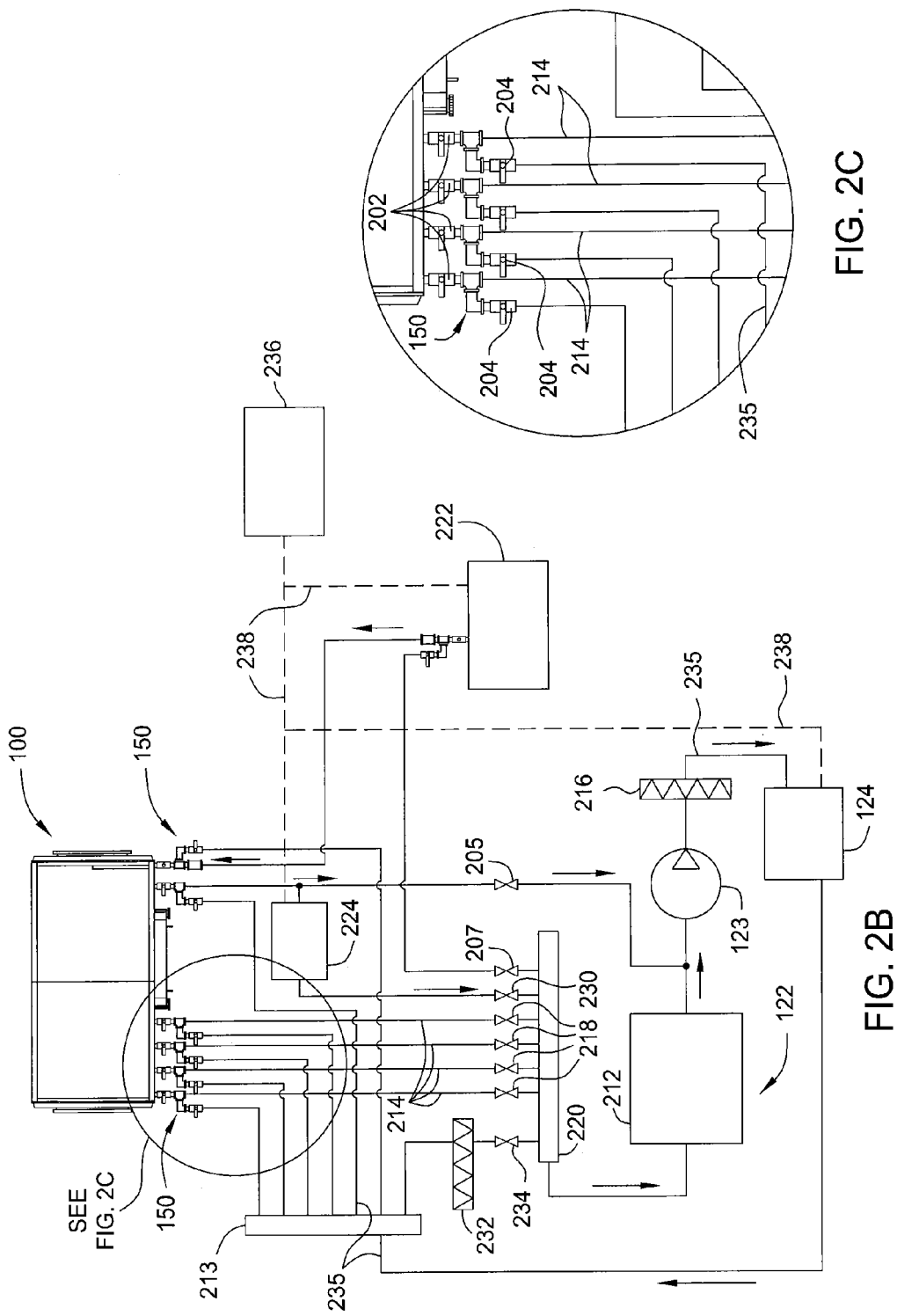

METHOD AND APPARATUS FOR IN-SITU TESTING OF FILTRATION SYSTEMS

CROSS-REFERENCE TO RELATED APPLICATIONS

This application is a continuation application of U.S. patent application Ser. No. 12/163,384, filed on Jun. 27, 2008, now U.S. Pat. No. 7,998,252, which claims benefit from the U.S. Provisional Patent Application Ser. No. 60/947,198, filed on Jun. 29, 2007, both of which are hereby incorporated by reference in their entireties.

BACKGROUND OF THE INVENTION

1. Field of the Invention

The embodiments described herein generally relate to an apparatus and method for certifying a filter in a containment system without decontaminating the containment system prior to certification. More particularly, embodiments described herein relate to containment housing isolatable from a sample system and a decontamination system thereby allowing for in-situ testing of a filter disposed in the housing.

2. Description of the Related Art

Numerous facilities handle hazardous and potentially fatal compounds and/or particles. These facilities include, for example, biological safety labs, pharmaceutical manufacturing facilities, biotechnology research labs, and production facilities. The hazardous particulates may include anything that is harmful or fatal to humans including, but not limited to, viruses, bacteria, chemicals, and waste products. Typically a containment system in the facility prevents the hazardous particles from escaping from the facility by filtering the air exiting hazardous areas prior to entering the surrounding environment.

The containment system typically consists of multiple components arranged in series. The components generally include one or more filter housing sections, one or more filters disposed in the one or more filter housing sections, an upstream test section, a downstream test section, and an air tight damper for isolating the containment system from the upstream and downstream ductwork that the containment system is coupled thereto.

The performance of the filters disposed in the containment system is critical to prevent human exposure to the hazardous particles. Therefore, it is necessary to certify the performance (e.g., leak and/or filtration efficiency) of the filters on a regular basis. The certification process ensures that the filters are meeting predefined operations criteria and/or standards. In-situ filter certification is often required for filters handling hazardous particles after the filters installation into the contamination housing. In-situ filter testing is performed by injecting an aerosol challenge upstream of the filter at a known concentration, flowing the aerosol laden air through the filter typically at an operational flow rate, and sampling the air downstream of the filter to determine at least one of a leak (such as pin-hole or edge) or an overall filtration efficiency of the filter based on a predefined filtering performance criteria.

There are two current methods for in-situ certification of a containment system. The first method uses two by-pass ports on the containment housing. A first port is upstream of the filter and a second port is located downstream from the filter. These ports are normally closed. To certify the filters, the containment system is turned off causing the facility to be shut down. The upstream and downstream dampers are closed while the inside of the containment housing is decontaminated by exposure to a decontamination agent. The ports are then opened to allow access to the filter during testing of the filter. The downstream damper and exhaust may be opened to allow the air and aerosol to pass through the filter. Since the containment system has been decontaminated and isolated from the upstream duct work, it is safe to test the filter in the containment system while allowing the air to flow through the exhaust and into the environment.

The second method for in-situ certification of the containment system uses air from the facility. This method requires the upstream and downstream dampers to be closed while the inside of the containment housing is decontaminated. When decontamination is complete the dampers open thereby allowing air from the lab or other work area into the containment system. An aerosol challenge is introduced into the air flowing through the filter to facilitate testing of the filter.

The methods described above are costly and time consuming. The testing process requires the facility and/or the containment system to be shut down during filter testing. The shutdown and decontamination may take several hours and even days in some cases. The loss of time of the facility during a decontamination may cost the facility millions of dollars due to lost research time or production time.

Therefore, there is a need for an improved method and apparatus for testing a filter in a containment system.

SUMMARY OF THE INVENTION

Embodiment described herein generally relate to a containment system. The containment system comprises a housing having an airflow inlet aperture and an airflow outlet aperture. The containment system further comprises a filter mounting portion disposed in the housing between the inlet and outlet apertures and configured to sealingly secure a filter in the housing in a position that filters air flowing between the apertures through the housing. The containment system further comprises a plurality of ports formed through the housing, wherein the ports include at least a downstream sample port and an upstream sample port. A first valve assembly is provided having a first port coupled to the upstream sample port, a second port, and a third port. A second valve assembly is provided having a first port coupled to one of the downstream sample ports, a second port, and a third port, wherein each of the valve assemblies have at least three operational states. The operational states comprise a first state preventing flow from the sample port from passing through the first port, a second state fluidly coupling the first and second ports, and a third state fluidly coupling the second and third ports.

Embodiment described herein generally relate to a method for testing a filter disposed in a containment system. The method comprises flowing air through a filter disposed in a containment housing and changing a state of a valve assembly coupled to a downstream sample port formed through the containment housing from a first state to a second state. The first state of the valve assembly prevents flow through the downstream sample port. The second state allows flow through the downstream sample port and valve assembly to a filter test equipment. The method further comprises testing the filter using samples provided to the filter test equipment through the sample port and changing the state of a valve assembly coupled to the downstream sample port from the second state to a third state, wherein the third state of the valve assembly allows flow of a decontamination agent through the filter test equipment and valve assembly.

BRIEF DESCRIPTION OF THE DRAWINGS

The accompanying drawings, which are incorporated in and constitute a part of the specification, schematically illustrate the present invention, and together with the general description given above and the detailed description given below, serve to explain the principles of the invention.

FIG. 1 depicts a section view of the containment system according to one embodiment.

FIG. 2B depicts a schematic view of a containment system coupled to a sample system and a decontamination system according to one embodiment.

FIG. 2C depicts a schematic view of a plurality of valve assemblies coupled to a containment system, a sample system and a decontamination system according to one embodiment.

To facilitate understanding, identical reference numerals have been used, where possible, to designate identical elements that are common to the figures. It is contemplated that elements of one embodiment may be beneficially incorporated in other embodiments without further recitation.

DETAILED DESCRIPTION

Figure 1:
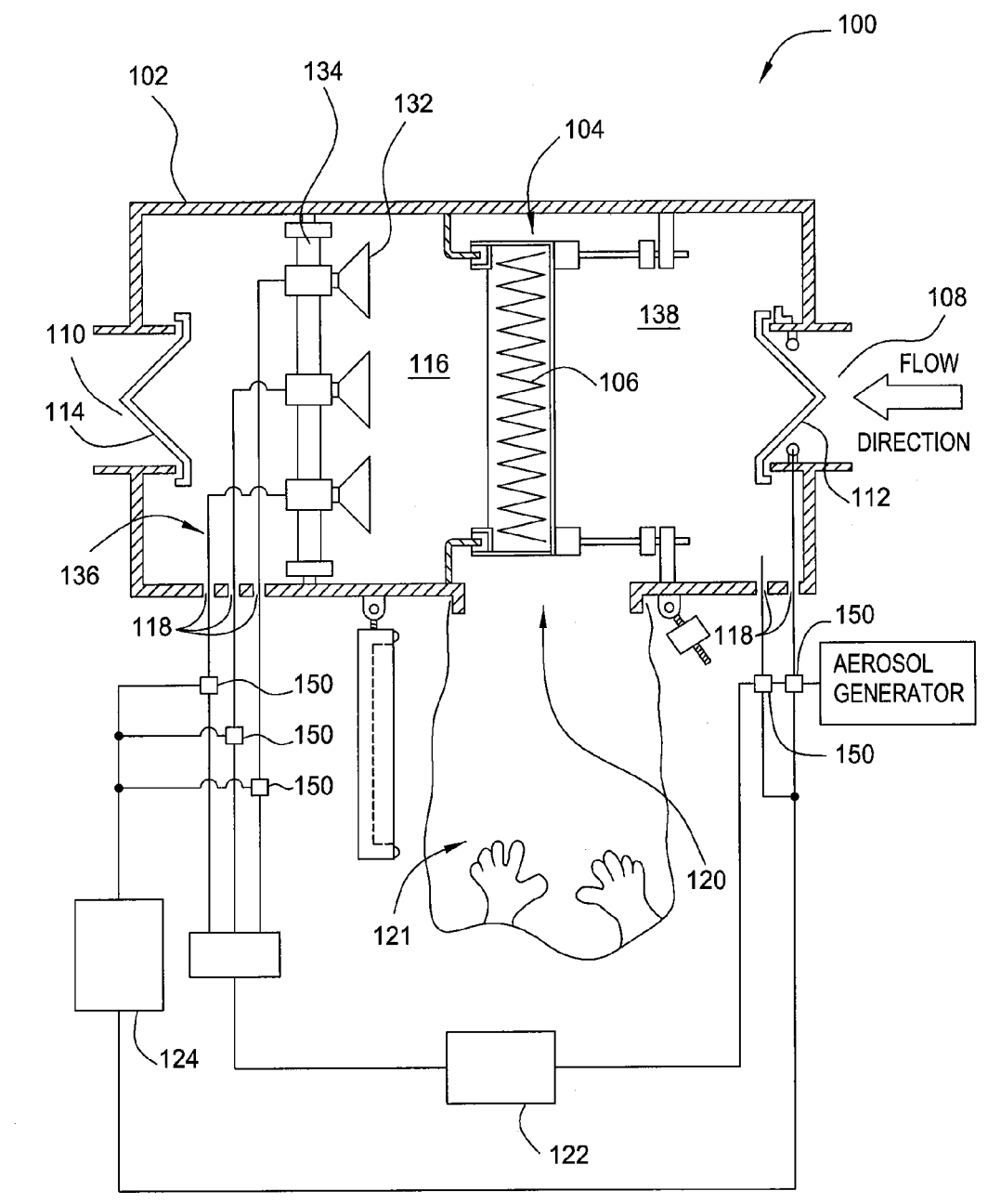
Figure 2A:
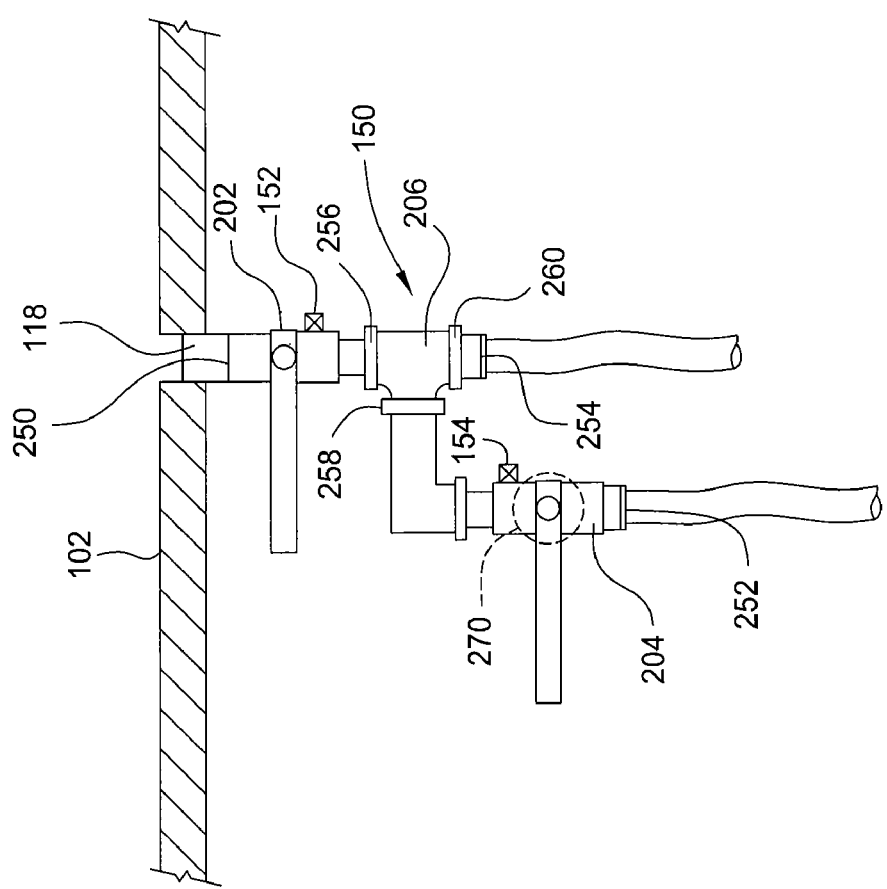
FIG. 2A depicts a view of one valve assembly according to one embodiment.

FIG. 1 is a sectional schematic view of a containment system 100. The containment system 100 ensures that air exiting or being recycled in a facility is substantially free of hazardous particles. The containment system 100 generally includes a housing 102 having one or more filters 106 disposed therein. One housing that may be adapted to benefit from the invention is described in United States Patent Publication No. 2007/0044438, filed Apr. 28, 2006, which is incorporated by reference. Another housing that may be adapted to benefit from the invention is a CAMCONTAIN™ Containment System, available from Camfil Farr, Inc., located in Washington, N.C. It is contemplated that other containment housings, including those available from other manufacturers, may be adapted to benefit from the invention.

In one embodiment, the housing 102 includes a filter mounting portion 104 for sealingly mounting the filter 106 to the housing, an airflow inlet aperture 108 and an airflow exit aperture 110. Each aperture 108, 110 has a damper 112, 114 for controlling the flow of air through the housing 102 and filter 106. In one embodiment, the dampers 112, 114 may be configured with a bubble-tight seal so that leakage may be prevented through the apertures 108, 110.

The housing 102 includes a sealable filter access port 120 formed through the housing 102 adjacent the filter mounting portion 104 to facilitate installation and replacement of the filter 106. As common practice, the sealable filter access port 120 includes a bag-in bag-out system 121 to prevent exposure of technicians to hazards during filter replacement.

The housing 102 also includes a test section 116 and a plenum section 138. The test section 116 is positioned downstream of the filter mounting portion 104 while the plenum section 138 is positioned upstream of the filter mounting portion 104. The test section 116 includes one or more downstream sample ports utilized to test the filter 106 disposed in the housing 102. The plenum section 138 is generally configured to provide sufficient space for mixing elements to provide an even distribution of aerosol challenge upstream of the filter 106.

A plurality of sample ports 118 are formed through the housing 102 to accommodate taking samples from the test section 116 and delivering aerosol to the plenum section 138. Each port 118 is fitted with a valve assembly 150. The valve assembly 150 is selectable between at least three states. In a first state, the valve assembly 150 prevents flow through the port 118. In a second state, the valve assembly 150 fluidly couples the port 118 to the test equipment necessary to test the filter 106 disposed within the housing 102, such as an aerosol generator, dilutor and sampling system 122. In a third state, the valve assembly 150 seals the port 118 but fluidly couples the test equipment to a decontamination system 124. The decontamination system 124, such may be part of the facility, generally provides an agent suitable for neutralizing hazardous agents that may be present in the test equipment after testing the filter 106. The decontamination system 124 may additionally be utilized to decontaminate the housing 102 prior to filter testing. The valve assembly 150 will be described in greater detail below.

In the embodiment depicted in FIG. 1, the downstream sample ports 118 disposed in the test section 116 comprises one or more probes 132 and a support structure 134. The support structure 134 couples the one or more probes 132 to the housing 102. The support structure 134 may statically hold the probes in a predefined position, or may be configured with one or more actuators, such as an x/y displacement mechanism, which dynamically positions (e.g., scans) the probe 132 along the downstream surface of the filter 106. The one or more probes 132 may have a design suitable for scan and/or efficiency testing. In one embodiment, the one or more probes 132 conform to IEST-RP-CC034.1 Recommended Practices.

The valve assembly 150 can be a single valve or a plurality of valves. The valve assembly 150 can have mechanical or automated actuation. The valve assembly 150 can include a manual or electronic lockout. The lockout prevents inadvertent actuation of the valve assembly 150. Further, the valve assembly 150 can have position sensors 152 (shown schematically) that provide the controller with a metric indicative of the state of the valve. The controller, in response to a metric, can electronically lockout the valve assembly 150 to prevent change in state of the assembly 150 so that the routing of gas flow through the valve assembly 150 cannot be changed. Further, the valve assembly 150 can have a sensor 154 (shown schematically) to determine if lines to the sample system 122 and/or decontamination system 124 are coupled to valve assembly 150 to prevent inadvertent actuation.

A valve assembly 150 is respectively coupled to a corresponding sample port 118, as shown in FIG. 2A-2C. The one or more valve assemblies 150 allow an operator to selectively control the flow between the test section 116, plenum section 138, the sample system 122, and the decontamination system 124. In one embodiment, each of the one or more valve assemblies 150 includes an isolation valve 202 and a decontamination valve 204. The valve assembly 150 alternatively may also be a single selector valve configured to seal the sample port 118, allow flow between the test section 116 and the sample system 122, the test section 116 and the decontamination system 124, or the decontamination system 124 and the sample system 122. The valve assemblies 150 can each comprise a first port 250, a second port 252 and a third port 254. The first port 250 fluidly couples the valve assembly 150 to the sample port 118. The second port 252 fluidly couples valve assembly 150 to the decontamination system 124. The third port 254 fluidly couples the valve assembly 150 to the sample system 122.

FIG. 2A depicts one embodiment of the valve assembly 150. The valve assembly 150 comprises an isolation valve 202 and a decontamination valve 204 configured to control flow between the test section, the sample system 122 and the decontamination system 124. The upstream of the isolation valve 202 is coupled to the port of the housing 102. The downstream side of the isolation valve 202 is coupled to a tee fitting 206 at a first tee port 256. The second side of the tee fitting 206 is coupled to the decontamination system 124 through the decontamination valve 204 at a second tee port 258. The third side of the tee fitting 206 is coupled to the sample system 122, at a third tee port 260.

The isolation valve 202 is in fluid communication with the corresponding sample port 118. The isolation valve 202 selectively isolates the sample system 122 from the test section 116 or the plenum section 138. As shown in FIGS. 2A-2C, the isolation valve 202 is in the closed position. In the closed position, the isolation valve 202 prevents fluid flow from exiting the test section 116 through the sample port 118.

The decontamination valve 204 is in fluid communication with the sample system 122. The decontamination valve 204 selectively isolates the decontamination system 124 from the tee fitting 206. As shown in FIGS. 2A-2C, the decontamination valves 204 are in the closed position. In the closed position, the decontamination valve 204 prevents fluid flow from the decontamination system 124 to the sample system 122.

In one embodiment, the isolation valve 202 and the decontamination valve 204, as shown in FIG. 2A-2C, are both hand operated ball valves. However, it is contemplated that any valve capable of selectively controlling and isolating flow may be used including, but not limited to, a single selector valve, a gate valve, a spool valve, a pneumatic valve, a solenoid valve, a control valve or other suitable flow control device. Although the valve assembly 150 is shown as being hand operated, it is contemplated that the valve assembly 150 may be automatically actuated to change the state of the valve. Thus, the operation of one or both of the isolation valve 202 and the decontamination valve 204 may be automatically controlled from a controller 236. For example, the valve and/or valves comprising one or more of the valve assemblies 150 may include an automatic actuator 270 (shown in phantom). The automatic actuator 270 may be a servo motor, a stepper motor, a rotary actuator, a pneumatic or hydraulic actuator, a linear actuator, solenoid or other actuator suitable for changing the state of the valve in response to a signal from the controller 236.

The valve assembly 150 may also include the sensor 152 and/or 154 that provides the controller 236 with a signal indicative of the position (i.e., flow state) and/or if the valve is connected to a conduit (so that fluids can not inadvertently exit the valve into surrounding environment), thus enabling a lockout if the valves are not properly sequenced or are in an unintended state. The lockout may be mechanical, or electronic. The sensors 152, 154 may be a flow sensor interfaced with the fluid conduits of the valve assembly, a proximate indicator configured to detect if the valve assembly 150 is coupled to appropriate conduits, or an encoder, limit switch or other sensor suitable for detecting the open and/or closed state of the one or more valves comprising the valve assembly 150.

In an alternative embodiment, one or both of the isolation valve 202 and the decontamination valve 204 may include a one-way (check) valve. The one-way valve associated with the isolation valve 202 may be arranged to allow fluid flow from the test section 116 to the sample system 122 while preventing flow in the opposite direction. The one-way valve associated with the decontamination valve 204 may be arranged to allow fluid flow from the decontamination system 124 to the sample system 122 while preventing flow in the opposite direction.

FIG. 2B depicts the containment system 100 coupled to the sample system 122, an aerosol generator 222 and the decontamination 124 system to facilitate in-situ testing of the filter 106 disposed in the housing 102. The decontamination system 124 selectively decontaminates the sample system 122, the aerosol generator 222, and/or the dilutor 224. The decontamination valves 204 may be selectively opened to allow a decontamination agent to enter the sample system 122. The isolation valve 202 is generally closed while the decontamination valve 204 is open. The isolation valves 202 selectively prevent the agents from the decontamination system 124 from entering the interior of the housing 102 through the sample ports 118. The decontamination system 124 circulates a sterilization (decontamination) agent through any of the systems to be decontaminated. As shown, the decontamination system 124 couples to the decontamination valves 204 via one or more decontamination lines 235. The decontamination lines 235 couple directly to the decontamination valves 204 or to an intermediate coupler, such as a decontamination manifold 213, between the decontamination valves 204 and the decontamination lines 235. The intermediate coupler may be any device for sealingly coupling the decontamination system 124 to the decontamination valve 204. For example, the intermediate coupler may be a quick connect. The intermediate coupler allows an operator to quickly couple the decontamination lines 235 to the decontamination valves 204.

The sterilization agent may be any sterilization agent used to decontaminate hazardous particles from containment systems including, but not limited to formaldehyde. The concentration of the sterilization agent and the duration of the decontamination cycle are a function of the sterilization agent used, the hazardous particles in the system, and other factors that may be specific to a particular application.

The aerosol generator 222 supplies an aerosol challenge to the upstream side of the filter 106 through at least one of the valve assemblies 150 coupled to the plenum section 138. The aerosol generator 222 provides an aerosol to the plenum section 138 of sufficient concentration to provide a statistically valid test of the filter 106. The aerosol generator 222 may be coupled to the sample manifold 220 through a decontamination return valve 207.

The sample system 122 measures the particles present in the air samples taken from the test section 116 and plenum section 138 of the containment system 100 through the sample ports 118 of that leak or efficiency determinations may be make. The sample system 122 includes a dilutor 224, a filter test equipment 212, one or more lines 214, and an exhaust filter 216. The one or more lines 214 convey the air samples to the filter test equipment 212. The filter test equipment 212 may be a photometer, particle counter, or other equipment suitable for leak and/or efficiency testing of the filter 106. The filter test equipment 212 provides a metric indicative of the number of particles present in the air samples. The measured air sample exiting the filter test equipment 212 is exhausted from the sample system 122 through the exhaust filter 216.

The dilutor 224 is also coupled to the upstream side of the filter 106 through at least one of the valve assemblies 150 coupled to the plenum section 138. The dilutor 224 is provided a sample of the air and aerosol present in the plenum section 138 through the valve assembly 150 when the isolation valve 202 is open and the decontamination valve 204 is closed. The dilutor 224 is configured to dilute the upstream sample a predefined amount so that the concentration of particles provided to the filter test equipment 212 of the sample system is within the operational limits of the filter test equipment 212 so that an upstream concentration limit may be calculated for use in determining the filtration efficiency and/or leak threshold.

The one or more lines 214 coupling the one or more valve assemblies 150 to the filter test equipment 212 may each be coupled to a solenoid valve 218 so that samples from each line may be sequenced through the filter test equipment 212. The solenoid valves 218 may be independently operated and controlled. In one embodiment, each solenoid valve 218 controls the flow from each line 214 into a sample manifold 220. The common outlet of the sample manifold 220 is fluidly coupled to the filter test equipment 212. In this embodiment, any one, or combination, of the solenoid valves 218 may open in order to test the air sample from that particular probe 132 (or dilutor 224) associated with the corresponding valve assembly 150.

A decay bypass valve 205 may be coupled to the upstream side of the filter 106 through at least one of the valve assemblies 150 coupled to the plenum section 138. In one embodiment, the decay bypass valve 205 couples the inlet of the dilutor 224 to the outlet of the filter test equipment 212. In this embodiment, the decay bypass valve 205 may open in order to allow more rapid evacuation of the housing and system when performing vacuum pressure decay tests.

In one embodiment, the air leaving the filter test equipment 212 passes through an exhaust filter 216. The exhaust filter 216 prevents an hazardous particles which may be within the sample system 122 from being passed to the environment after sampling. The exhaust filter 216 may be any suitable filter.

The sample system 122 may optionally include a vacuum pump 123 or compressor (not shown). The pump 123 aides in circulation of the air sample and/or a sterilization agent from the decontamination system 124 through the sample system 122. Any suitable pump or compressor may be used so long as the pump or compressor is compatible the sterilization agent.

A bypass filter 232 may be coupled to the sample manifold 220. The bypass filter 232 may be any suitable filter, for example a HEPA filter. Air flow from the bypass filter 232 to the sample manifold 220 can be selectively controlled by a bypass valve 234. As shown, the bypass valve 234 is a solenoid valve, but may be any suitable valve. The bypass filter 232 provides air to the filter test equipment 212 when the solenoid valves 218 interfaced with the one or more lines 214 are closed. The bypass filter 232 allows the pump or compressor of the filter test equipment 212 to continue to circulate air. This prevents the pump or compressor from failing, thereby extending the service life of the filter test equipment 212.

Referring primarily to FIG. 2B, the controller 236 includes control lines 238 for communicating with the various components of the sample system 122, the decontamination system 124, the valve assemblies 200, the solenoid valves 218, 230 and/or 234, the dilutor 224, and/or the aerosol generator 222. The controller 236 sends and receives data via the control lines 238. Optionally, the controller 236 may communicate using fluid, pneumatic, and/or wireless (e.g., infrared, RF, Bluetooth, etc.) signals with components described herein. The controller 236 may be configured to operate and monitor each of the respective components in an automated fashion (e.g., according to a preprogrammed sequence stored in memory) or according to explicit user input.

Although not shown, the controller 236 may be equipped with a programmable central processing unit, a memory, a mass storage device, and well-known support circuits such as power supplies, clocks, cache, input/output circuits, and the like. Once enabled, an operator may control the operation of the containment system 100, the sample system 122, the decontamination system 124, the aerosol generator 222 and the dilutor 224 by inputting commands into the controller 236. To this end, another embodiment of the controller 236 includes a control panel, not shown. The control panel may include a key pad, switches, knobs, a touch pad, etc. The controller 236 may further comprise a visual display.

Figure 3:
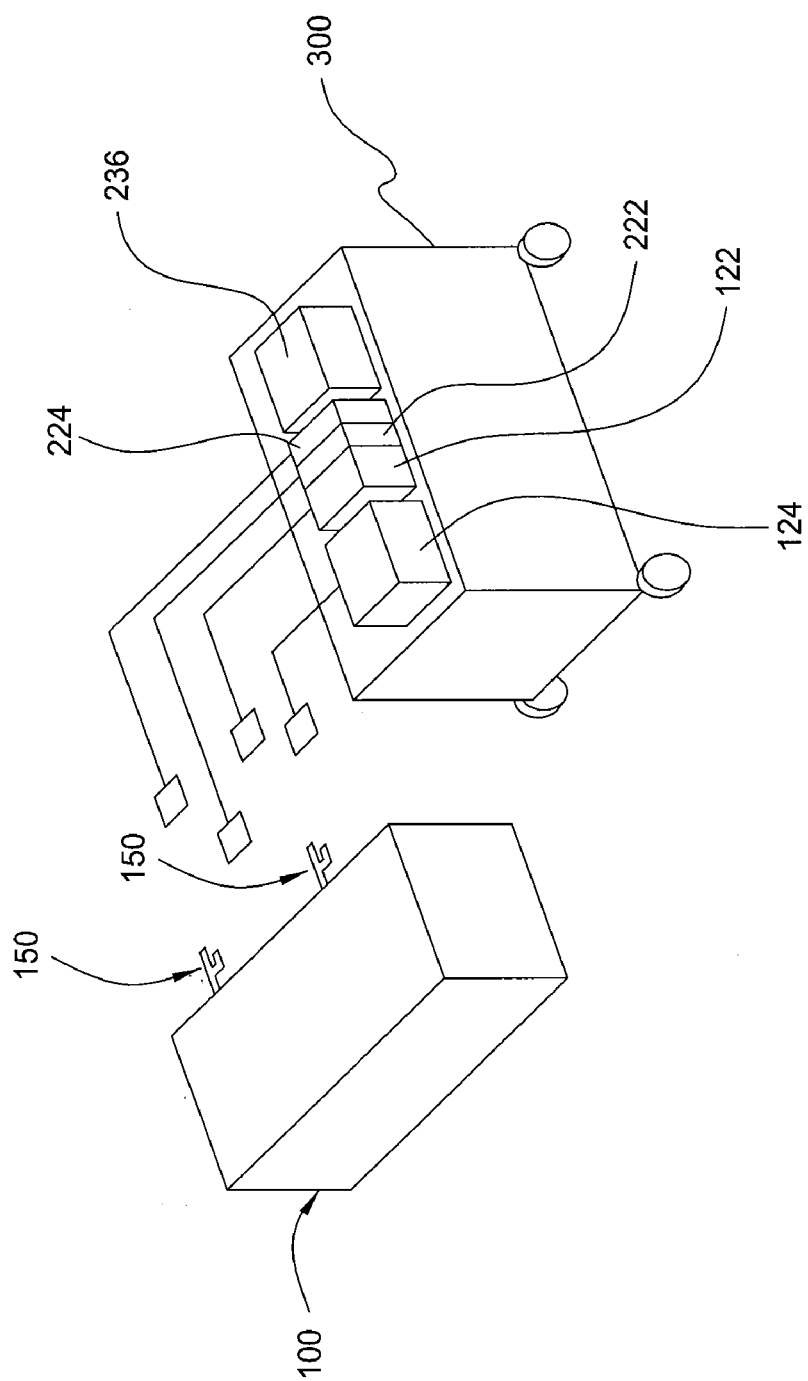
FIG. 3 depicts a transporter according to one embodiment.

FIG. 3 depicts a transporter 300. The transporter 300 allows components of the sample system 122 and, in some embodiments, the decontamination system 124, to be easily moved to and from the containment system 100 to facilitate testing and certification. The transporter 300 may include any combination of the sample system 122, the decontamination system 124, the controller 236 and/or the aerosol generator 222. For example, the transporter 300, as shown, carries the sample system 122, including the aerosol generator 222 and the dilutor 224, the decontamination system 124, and the controller 236. In another embodiment, the sample system 122 and the decontamination system 124 are on separate transporters 300. The transporter 300 shown is a cart; however, it should be appreciated that the transporter 300 may be any suitable device capable of carrying the component including, but not limited to, a bag, a suitcase, a backpack, a skid, a trailer, or a human.

During normal operation of the containment system 100 the valve assemblies 150 are in the first state. In the first state, the valve assemblies 150 prevent flow through the ports 118. In one embodiment, the isolation valve 202 is closed in the first state. The first state allows the containment system 100 to filter facility air through the housing 102 without contaminating the sample system 122. The valve assembly 150 remains in the first state until a filter test and/or certification is desired. When the filter test is desired, the sample system 122 is coupled to the valve assemblies 150. The sample system 122 may be moved proximate to the containment system 100 via the transporter 300. In an alternative, the sample system 122 can already be coupled to and/or a part of the containment system 100.

To test the filter 106, the valve assemblies 150 are placed in the second state. In the second state, the valve assemblies 150 fluidly couple the ports 118 to the filter test equipment 212 of the sample system 122 that are necessary to test the filter 106 disposed within the housing 102. In one embodiment, the second state is achieved by opening the isolation valve 202 while the decontamination valve 204 remains closed An aerosol challenge is provided by the aerosol generator to the plenum section of the housing 102 through the appropriate valve assembly 150. After the upstream challenge concentration has stabilized within the housing, the appropriate solenoid valve 218 is opened to allow the dilutor 224 to provide a sample to the filter test equipment 212 so that the upstream concentration and/or leak threshold may be established. The appropriate solenoid valves 218 are actuated to provide downstream samples obtained through the probes 132 to the filter test equipment 212. From the downstream samples, the filter efficiency and/or location of a leak may be determined. The pump or compressor of the filter test equipment 212 can pull the air sample from the test section 116. The air sample travels via the one or more tubes 136 through the wall of the housing 102 and through the one or more valve assemblies 150. The air sample travels past the valve assemblies 150 and into the one or more lines 214 of the sample system 122. The decontamination system 124 remains isolated from the sample system 122. This prevents the flow of the air sample into the decontamination system 124 while causing the air sample to enter the sample system 122.

The air sample travels to the filter test equipment 212 for testing. The filter test equipment 212 tests the air sample. The filter test equipment 212 can directly store and/or convey the information from the test to an operator or the controller 236 via the control lines 238. The air sample exhausts from the filter test equipment 212 through the exhaust filter 216. The exhaust filter 216 may recirculate the filtered air sample back into the facility, the housing 102, or the decontamination system 124. This process continues until the test is complete.

Advantageously, the in-situ testing of the filter is completed without decontaminating the housing 102. By not decontaminating the housing prior to testing, significant time is saves which can be utilized for operational activities of the facilities. Moreover, since the large volume of the housing is not exposed to decontamination agents, the amount of decontamination agents utilized is significantly reduced.

Upon completion of the filter test, the valve assemblies 150 are actuated to the third state. In the third state, flow is prevented through the valve assembly 150 into the housing 102, while flow is provided between the decontamination system and the sample system. Selectively, the dilutor 224, aerosol generator 222, sample manifold 220 and filter test equipment 212, and exhaust filter 216 may be exposed to the decontamination agents.

An operator or the controller 236 may be utilized to actuate the valve assemblies 150. In one embodiment, the third state includes having the decontamination valve 204 in an open state while the isolation valve 202 is a closed state. To decontaminate the sample system 122, the sterilization agent flows from through the decontamination valve 204 and into the one or more valve assemblies 150 into the sample system 122. The solenoid valves 218 are held in an open state or cycled open and closed. The dilutor 224, and optionally, the aerosol generator 222 are decontaminated in as described above. The isolation valve 202 remains closed thereby preventing the flow of the sterilization agent into the housing 102. The sample system 122 may circulate the sterilization agent in the same manner as the air samples. Thus, the sterilization agent flows through all of the potentially contaminated components of the sample system 122, the aerosol generator 222, and the dilutor 224 while the containment system remains in an operational state, thereby contributing to the cost effective operation of the facility. The sterilization agent may be recirculated back into the decontamination system 124. The duration of the decontamination process is a function of the hazardous particles to be decontaminated. With the decontamination complete the valve assemblies 150 may return to the first state. The decontamination lines 235 can uncouple from the one or more valve assemblies 150. The decontamination system 124 and/or the sample system 122 may then be moved to another housing 102 of the same or a separate containment system 100. The process may be repeated to certify another filter.

The embodiments described herein enable HEPA and carbon filters in containment, glove box, biological safety cabinets, transfer units and other filtration systems to be certified for leaks via scan testing and/or overall efficiency testing without having to decontaminate or sterilize the housing in which the filter is installed prior to conducting filter certification. This eliminates the need to decontaminate or sterilize, laboratories, work spaces, clean spaces, production areas, glove boxes, clean benches or other areas or systems serviced by the containment and filtration systems described above. This is advantageous in that it reduces facility down-time associated with having to decontaminate systems or areas listed above. Reducing the facility down time can equate to higher yields, production capacity, profitability or experiment duration. Further, the system provides a cost-effective method to certify filters after an "upset" condition without having to shut down the experiment and potentially lose months or even years worth of time, money and investment, as well as eliminating potential adverse impacts on socially critical experiments or processes.

While the foregoing is directed to embodiments of the present invention, other and further embodiments of the invention may be devised without departing from the basic scope thereof, and the scope thereof is determined by the claims that follow.

What is claimed is:

1. A containment system, comprising:
    a housing having an airflow inlet aperture and an airflow outlet aperture;
    a filter mounting portion disposed in the housing between the inlet and outlet apertures and configured to sealingly secure a filter in the housing in a position that filters air flowing from the inlet aperture to the outlet aperture through the housing;
    a plurality of ports formed through the housing, wherein the plurality of ports include at least a downstream sample port and an upstream sample port;
    a first valve assembly having a first port coupled to the upstream sample port, a second port, and a third port, and
    a second valve assembly having a first port coupled to one of the downstream sample port, a second port, and a third port,
    wherein each of the valve assemblies have at least three operational states, wherein the operational states comprise:
        a first state preventing flow from the sample port from passing through the first port;
        a second state fluidly coupling the first and second ports; and
        a third state fluidly coupling the second and third ports.

2. The containment system of claim 1, wherein each of the valve assemblies further comprises:
    an isolation valve having an inlet port and an outlet port, wherein the inlet port is the first port of the valve assembly; and
    a decontamination valve having an inlet port and an outlet port, wherein the inlet port is the second port of the valve assembly and wherein the outlet port of the decontamination valve is coupled to the outlet port of the isolation valve.

3. The containment system of claim 2, further comprising:
    a tee having a first, second, and third tee port, wherein the third tee port is the third port of the valve assembly and wherein the second tee port of the tee is coupled to the outlet port of the decontamination valve and the first tee port of the tee is coupled to the outlet port of the isolation valve.

4. The containment system of claim 1, further comprising:
    a filter testing device coupled to the downstream sample port through the second valve assembly; and
    a decontaminant source coupled to the downstream sample port through the second valve assembly.

5. The containment system of claim 1, further comprising:
    a dilutor coupled to the upstream sample port through the first valve assembly; and
    a decontaminant source coupled to the upstream sample port through the first valve assembly.

6. The containment system of claim 1, wherein the second valve assembly comprises a single selector valve.

7. The containment system of claim 1, wherein the second valve assembly comprises a plurality of valves.

8. The containment system of claim 1 further comprising:
    a controller coupled to at least one of the first and second valve assemblies and enabling a change in state of each of the valve assemblies in response to metric provided by at least one sensor, wherein the metric is indicative of at least one of the state of each valve assembly or presence of a conduit coupled to the ports of each valve assembly.

9. A containment system, comprising:
a housing having an airflow inlet aperture and an airflow outlet aperture;
a filter mounting portion disposed in the housing between the inlet and outlet apertures and configured to sealingly secure a filter in the housing in a position that filters air flowing from the inlet aperture to the outlet aperture through the housing;
at least one sample port formed through the housing; and
at least one valve assembly having a first port coupled to the sample port, a second port, and a third port, and wherein the valve assembly has at least three operational states, wherein the operational states comprise:
a first state preventing flow from the sample port from passing through the first port;
a second state fluidly coupling the first and second ports; and
a third state fluidly coupling the second and third ports.

10. The containment system of claim 9, wherein the valve assembly further comprises:
an isolation valve having an inlet port and an outlet port, wherein the inlet port is the first port of the valve assembly; and
a decontamination valve having an inlet port and an outlet port, wherein the inlet port is the second port of the valve assembly and wherein the outlet port of the decontamination valve is coupled to the outlet port of the isolation valve.

11. The containment system of claim 10, further comprising:
a tee having a first, second, and third tee port, wherein the third tee port is the third port of the valve assembly and wherein the second tee port of the tee is coupled to the outlet port of the decontamination valve and the first tee port of the tee is coupled to the outlet port of the isolation valve.

12. The containment system of claim 9, wherein the sample port comprises a downstream sample port disposed downstream of the filter mounting portion; and wherein the containment system further comprises:
a filter testing device coupled to the downstream sample port through the valve assembly; and
a decontaminant source coupled to the downstream sample port through the valve assembly.

13. The containment system of claim 9, wherein the sample port comprises an upstream sample port disposed upstream of the filter mounting portion; and wherein the containment system further comprises:
a dilutor coupled to the upstream sample port through the valve assembly; and
a decontaminant source coupled to the upstream sample port through the valve assembly.

14. The containment system of claim 9, wherein the valve assembly comprises a single selector valve.

15. The containment system of claim 9, wherein the valve assembly comprises a plurality of valves.

16. The containment system of claim 9, further comprising:
a controller coupled to the valve assembly and enabling a change in state of the valve assembly in response to metric provided by at least one sensor, wherein the metric is indicative of at least one of the state of the valve assembly or presence of a conduit coupled to the ports of the valve assembly.

17. A containment system, comprising:
a filter housing having an airflow inlet port, an airflow outlet port, a filter access port configured with a bagging ring, a downstream sample port, and a valve assembly, where in the valve assembly is operable between states that prevent flow through the downstream sample port, opens the downstream sample port to a sampling flow path, and opens the downstream sample port to a decontaminant flow path.

18. The containment system of claim 17, wherein the sampling flow path is coupled to a device configured to test the filter.

19. The containment system of claim 17, wherein the decontaminant flow path is coupled to a decontaminant generator.

* * * * *